US009678026B2

(12) United States Patent
Lenczowski

(10) Patent No.: US 9,678,026 B2
(45) Date of Patent: Jun. 13, 2017

(54) STRUCTURAL HEALTH MONITORING SYSTEM FOR A MATERIAL AND PRODUCTION METHOD

(71) Applicant: Airbus Defence and Space GmbH, Ottobrunn (DE)

(72) Inventor: Blanka Lenczowski, Neubiberg (DE)

(73) Assignee: Airbus Defence and Space GmbH, Ottobrunn (DE)

( * ) Notice: Subject to any disclaimer, the term of this patent is extended or adjusted under 35 U.S.C. 154(b) by 303 days.

(21) Appl. No.: 14/481,101

(22) Filed: Sep. 9, 2014

(65) Prior Publication Data

US 2015/0071324 A1 Mar. 12, 2015

(30) Foreign Application Priority Data

Sep. 10, 2013 (DE) .................... 10 2013 014 822

(51) Int. Cl.
| | |
|---|---|
| *G01N 25/72* | (2006.01) |
| *G01M 5/00* | (2006.01) |
| G01L 19/00 | (2006.01) |
| G01F 1/68 | (2006.01) |
| B64G 1/56 | (2006.01) |
| G01R 31/08 | (2006.01) |
| G01M 9/06 | (2006.01) |

(52) U.S. Cl.
CPC .......... *G01N 25/72* (2013.01); *G01M 5/0016* (2013.01); *G01M 5/0025* (2013.01); *G01M 5/0033* (2013.01); *G01M 5/0083* (2013.01); *B64G 1/56* (2013.01); *G01F 1/68* (2013.01); *G01L 19/0007* (2013.01); *G01M 9/065* (2013.01); *G01R 31/08* (2013.01)

(58) Field of Classification Search
CPC ........................................................ B64G 1/56
USPC ............................................ 73/432.1; 374/45
See application file for complete search history.

(56) References Cited

U.S. PATENT DOCUMENTS

| | | | | |
|---|---|---|---|---|
| 7,786,736 | B2 * | 8/2010 | Thostenson ......... | B29C 47/0004 |
| | | | | 324/525 |
| 8,684,595 | B2 * | 4/2014 | Wardle .................. | B82Y 15/00 |
| | | | | 374/45 |
| 9,091,657 | B2 * | 7/2015 | Kessler ................. | G01N 25/72 |
| 9,194,832 | B2 * | 11/2015 | Dunleavy .............. | B82Y 30/00 |
| 2005/0036905 | A1 * | 2/2005 | Gokturk ................ | B82Y 15/00 |
| | | | | 422/400 |

(Continued)

FOREIGN PATENT DOCUMENTS

| | | |
|---|---|---|
| EP | 1 600 231 A1 | 11/2005 |
| EP | 2 431 412 A1 | 3/2012 |

(Continued)

OTHER PUBLICATIONS

European Search Report, EP14002973, European Patent Office, 15, Jan. 2015, 5 pages.*

(Continued)

*Primary Examiner* — Clayton E Laballe
*Assistant Examiner* — Kevin Butler
(74) *Attorney, Agent, or Firm* — Crowell & Moring LLP

(57) ABSTRACT

A structural health monitoring system includes a signal transmission element and a sensor unit. The sensor unit is designed to feed a first signal into the signal transmission element and to read out a second signal from the signal transmission element. The signal transmission element has carbon nanotubes.

14 Claims, 2 Drawing Sheets

(56) References Cited

U.S. PATENT DOCUMENTS

| | | | |
|---|---|---|---|
| 2005/0284232 A1* | 12/2005 | Rice | G01B 7/18 |
| | | | 73/762 |
| 2007/0138010 A1* | 6/2007 | Ajayan | G01L 1/005 |
| | | | 204/400 |
| 2007/0166831 A1* | 7/2007 | Watkins, Jr. | G01N 27/041 |
| | | | 436/149 |
| 2007/0222472 A1* | 9/2007 | Raravikar | B82Y 10/00 |
| | | | 73/774 |
| 2010/0096183 A1* | 4/2010 | Rice | G01M 5/0016 |
| | | | 174/70 C |
| 2011/0089958 A1* | 4/2011 | Malecki | B82Y 30/00 |
| | | | 324/693 |
| 2011/0142091 A1* | 6/2011 | Wardle | B82Y 15/00 |
| | | | 374/45 |
| 2011/0240621 A1* | 10/2011 | Kessler | G01N 25/72 |
| | | | 219/200 |
| 2015/0071324 A1* | 3/2015 | Lenczowski | G01N 25/72 |
| | | | 374/45 |

FOREIGN PATENT DOCUMENTS

| | | |
|---|---|---|
| WO | WO 2009/141100 A1 | 11/2009 |
| WO | WO 2011/094347 A2 | 8/2011 |

OTHER PUBLICATIONS

German Office Action dated Apr. 23, 2014 (five pages).
German-language European Search Report dated Jan. 22, 2015 with partial English translation (eight pages).

* cited by examiner

STRUCTURAL HEALTH MONITORING SYSTEM FOR A MATERIAL AND PRODUCTION METHOD

CROSS-REFERENCE TO RELATED APPLICATIONS

The present application claim priority under 35 U.S.C. §119 to German application 10 2013 014 822.7, filed Sep. 10, 2013, the entire disclosure of which is herein expressly incorporated by reference.

FIELD OF THE INVENTION

Exemplary embodiments of the invention relate to a structural health monitoring system for a material, a material with a structural health monitoring system as well as a method for producing such a material.

BACKGROUND OF THE INVENTION

The properties of materials, which are used in a complex, higher level overall structure, can be subject to monitoring, for example, in order to obtain a periodically recurrent overview of the properties of the monitored material. In particular, the mechanical and physical properties of a material, for example, the strength, residual strength, fatigue, E-modulus, are the target of such structural health monitoring measures.

Structural health monitoring systems are used to monitor the properties, in particular, the mechanical properties, of a material. In the case of complex systems, which are subject to high loads as well as stringent safety requirements, a permanent monitoring of the structural health can contribute to a flexible adjustment of a maintenance cycle of these complex systems and, as a result, to an extended service life and higher reliability of such materials.

A known structural health monitoring device works with ultrasound. In this case ultrasound heads are subsequently mounted on a component by means of an adhesive bond. The reflected ultrasound can vary as a function of the structure of a material, a feature that allows, for example, conclusions to be drawn about cracks or other mechanical damages in the structure of the tested material.

In the case of metal structures, such as components of airplanes or industrial plants, it is possible to use not only acoustical, but also optical methods for testing structures.

SUMMARY OF THE INVENTION

If structural health monitoring systems are applied to a material as additional applications, then the result may be an additional weight, which may be undesired, depending on the field of application of the material.

In the case of ultrasound heads, which are adhesively cemented on a material, the bonding joint may form, for example, a weak point, especially if significant environmental impacts, such as temperature variation, or mechanical loads, such as expansions or vibrations, occur, which are adverse impacts that can subject both the ultrasound heads and the bonding surface to a high load.

Due to their operating mode such ultrasound heads can have the drawback that they allow only a limited local inspection of the material.

Therefore, the exemplary embodiments of the present invention are directed to a structural health monitoring system and a method for producing a material with such a structural health monitoring system, wherein the structural health monitoring system has a low weight and enables a reliable monitoring of a structure of the material.

According to one aspect, a structural health monitoring system is provided for a material. The structural health monitoring system has a signal transmission element and a sensor unit. The sensor unit is designed to feed a first signal into the signal transmission element and to read out a second signal from the signal transmission element. The structural health monitoring system is characterized in that the signal transmission element has carbon nanotubes.

Such a structural health monitoring system can be used in carrying or supporting structures with a functional capability of transmitting signals within the framework of monitoring the structure.

For example, the structural health monitoring system can be used to monitor industrial plants, airplane components, pipelines or components of wind power plants or, in general, to monitor mechanically stressed or mechanically loaded components.

The sensor unit can have a signal generator and a signal receiver. The signal generator can be designed to feed a signal, for example, an electrical signal, into the signal transmission element. The signal receiver is designed to receive the signal that is fed in by the signal generator. Then conclusions about the structural damages of the material can be drawn, as a function of the signal received from the signal generator.

The signal, which is fed in by the signal generator, can be changed, for example, by the structural damages, like cracks or fractures, in the signal transmission element, for example, in that the amplitude of the signal strength varies in its entirety or only in certain frequency ranges. Such a variation in the signal enables the user to draw exact conclusions about the local area in which the damages have occurred and the extent to which the signal transmission element is damaged.

If the signal transmission element is disposed on or in a material, then the damages of the material are transmitted directly to the signal transmission element. Hence, the damages of the signal transmission element correspond to those of the monitored material; and these damages are determined by means of the structural health monitoring system, as described above and in the following.

In other words, the signal transmission element is used for transmitting a signal, in particular, an electrical or thermal signal. The signal is fed in by a signal generator and is received by a signal receiver. Any deviations of the received signal from the fed-in signal can be used to draw exact conclusions about the structure or more specifically the change in the structure of the signal transmission element. Hence, the changes in the structure of the signal transmission element correspond to the changes in the structure of the material or more specifically correspond to the damages of the material.

The signal transmission element includes carbon nanotubes. The carbon nanotubes are distinguished by a high electrical and thermal conductivity and, in addition, can also increase the mechanical load carrying capacity of the material, on which or in which the carbon nanotubes are affixed, due to the mechanical strength of the carbon nanotubes. In addition, carbon has a lower density than, for example, copper, silver or diamond and, as a result, leads to less additional weight, an aspect that can be very advantageous with respect to the monitoring of and/or the integration in airplane components.

Carbon nanotubes are tubular structures, which are made of carbon and have a diameter that can range between a few tenths of a nanometer (nm) and 50 nm. The length of a single tube can be up to a few millimeters (mm). Several single tubes can be combined together to form tube bundles.

The signal transmission element can have a plurality of tube bundles, which are constructed, for example, in a reticular manner or in the form of a honeycomb.

The signal transmission element can include carbon or carbon nanotubes (CNT) in the form of graphenes, aerographite, CNT yarn or so-called buckypaper.

When integrated into a material, the structural health monitoring system allows, as described above and in the following, the condition to be monitored during the operating period or the period of use and starting from sensor elements by means of electronic components for signal processing up to the linkage of subsystems and their incorporation in complex structural health monitoring devices, which have a plurality of structural health monitoring systems, as described above and in the following.

The structural health monitoring system makes it possible to detect significant changes in the structural behavior in that the signals, which are transmitted by way of the signal transmission element, are fed to an evaluation unit and/or assessment device. The use of this structural health monitoring system for monitoring safety relevant, complex metal structures or fiber composite structures in the period of time, during which these structures are used, can help to significantly reduce the amount of waiting time or rather to significantly decrease the idling of the monitored structures or more specifically the monitored materials and can significantly improve by early damage detection their efficiency over the entire service life or rather over the period of time, during which they are used.

It must be pointed out that the second signal is the first signal, which is transmitted over the signal transmission element. In other words, the first signal is, therefore, the input signal; and the second signal is the output signal.

According to one embodiment, the first signal and the second signal contain in each case an electrical signal component, wherein a ratio of the first signal to the second signal is used to determine an electrical transmission function of the signal transmission element.

As an alternative to the electrical transmission function, the electrical conductivity can also be determined. Changes in the electrical conductivity between an infeed point and a tapping point of the electrical signal indicate a change in the structure of the signal transmission element, a feature that is used as an indication of a change in the structure of the material. As a result, material damages can be detected at an early stage.

The first signal and the second signal can be used to determine a transmission function in the time range and/or frequency range of the signal transmission element. Variations in this transmission function in the time range and/or frequency range is indicative of changes in the structure of the signal transmission element.

According to an additional embodiment, the first signal and the second signal can contain in each case a thermal signal component, wherein a ratio of the first signal to the second signal is used to determine a thermal transmission function of the signal transmission element.

The statements with respect to the electrical transmission function apply in an analogous manner to the thermal transmission function, with the one difference that a thermal signal is used, instead of an electrical signal.

According to an additional embodiment, the signal transmission element has a plurality of transmission lines made of carbon nanotubes. In this case at least one transmission line is coupled to the sensor unit.

A first end section of a transmission line can be coupled to the signal generator; and a second end section of the same or another transmission line can be coupled to the signal receiver. In this case the first end section is coupled to the second end section by means of the plurality of transmission lines, so that the first signal is fed in by means of the first end section; and the second signal is read out by means of the second end section.

According to another embodiment, a first transmission line crosses a second transmission line, so that the signal transmission element is formed in a reticular manner.

According to an additional embodiment, the signal transmission element is designed as a continuous surface.

In this embodiment the signal transmission element is introduced on or in a material as a layer.

According to another aspect, a material is provided with a structural health monitoring system, as described above and in the following.

The structure of the material can be monitored by affixing a structural health monitoring system, so that damages, caused by mechanical loads on the material, or even changes in the structure due to forces, applied to the material, can be detected in the period of time, during which the material is used.

The structural health monitoring system can be applied to a surface of the material or can be integrated in the material. In the former case the structural health monitoring system can be retrofitted on the existing materials.

The sensor unit with the signal generator and the signal receiver are mounted on the material and coupled electrically and/or thermally to the signal transmission element.

According to one embodiment, the signal transmission element is disposed on a surface of the material.

The signal transmission element can cover the surface of the material in the form of lines or conducting tracks or can cover a wide area of the surface of the material on a subsection or even the entire surface.

In this embodiment it is possible to detect, in particular, damages of the surface of the material.

According to one embodiment, the signal transmission element is disposed in a surface layer of the material.

In other words, the signal transmission element is integrated in the material of the material. The surface layer can have a depth ranging from a few micrometers ($\mu$m) to some millimeters (mm). The signal transmission element penetrates the surface layer or more specifically passes through the surface layer.

This embodiment enables a detection of the damages, which are located under the surface of the material.

According to one embodiment, the signal transmission element is distributed over the entire material thickness of the material.

The signal transmission element penetrates the whole material. As a result, damages or more specifically changes in the structure of the material can be detected over the entire thickness of the material.

The signal transmission element can be disposed, as a filler, in substrates or materials. For example, the signal transmission element can be disposed in cavities, which occur in the material of the material.

In an additional embodiment the signal transmission element can be disposed as an additional layer between two adjacent material sheets or layers. The signal transmission element can be rolled in individually or as a mixture, such as in the form of a weld filler material, between the sheets or layers of the material.

According to another aspect, a method for producing a material, as described above and in the following, is provided. The signal transmission element is applied to the material or more specifically is incorporated in the material by means of a method from the group comprising rolling in, adhesive bonding and spraying.

When the signal transmission element is rolled in, it can be rolled onto the surface or can be rolled into a surface layer.

In the case of adhesive bonding, a film can be glued; or the adhesive bonding may be a coating system.

According to an additional aspect, the signal transmission element is used as a weld filler material or as a powder metallurgy preform material in the production of the material.

According to an additional embodiment, the signal transmission element is infiltrated in the structure of the material.

According to another embodiment, the signal transmission element is sewn, woven or knitted into the material and/or into the structure of the material.

According to an additional embodiment, the signal transmission element is applied to the material as a coating layer.

According to another embodiment, the signal transmission element is deposited by precipitation on the substrate.

According to an additional embodiment, the signal transmission element is stirred individually or as a weld filler material into the surface of the workpiece or into the friction stir weld seams.

Some examples of the embodiment of the invention are described below with reference to the drawings.

BRIEF DESCRIPTION OF THE FIGURES

The representations in the figures are shown in schematic form and are not drawn true to scale. If identical reference numerals are used in the following figures, then the reference numerals relate to identical or similar elements.

DETAILED DESCRIPTION OF THE EMBODIMENTS

Figure 1:
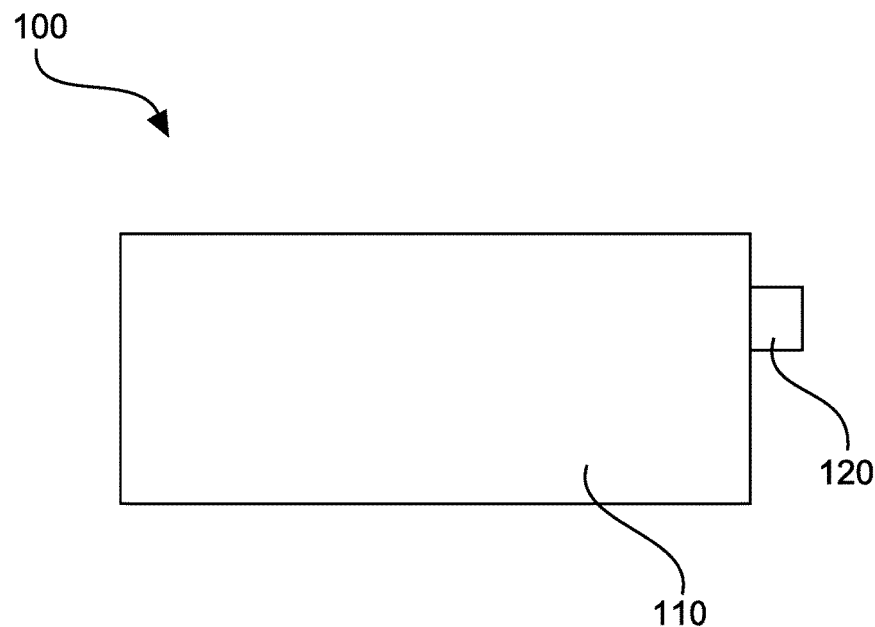
FIG. 1 shows a schematic representation of a structural health monitoring system according to one embodiment, shown as an example.

FIG. 1 shows a structural health monitoring system 100 comprising a signal transmission element 110 and a sensor element 120. The sensor element 120 is coupled to the signal transmission element 110, so that at least one electrical signal and/or one thermal signal can be fed into the signal transmission element 110 and can be read out of the signal transmission element. For this purpose the signal is fed in and read out at different locations, so that the signal transmission element acts with the transmission function on the signal that is fed in.

Changes in the structure of the signal transmission element 110 cause a change in the transmission function, so that these structural changes can be detected.

In FIG. 1 the signal transmission element is shown as a flat element, which can be applied, for example, to a surface of a material.

As an alternative, the signal transmission element can also have a plurality of lines or line sections, which are connected to each other in a reticular manner or in a honeycomb manner, in order to guide or more specifically to transmit the fed-in signal onto the specified paths. In such a scenario the structural changes, such as cracks, in the signal transmission element can also result in a complete break in the signal transmission.

Figure 2:
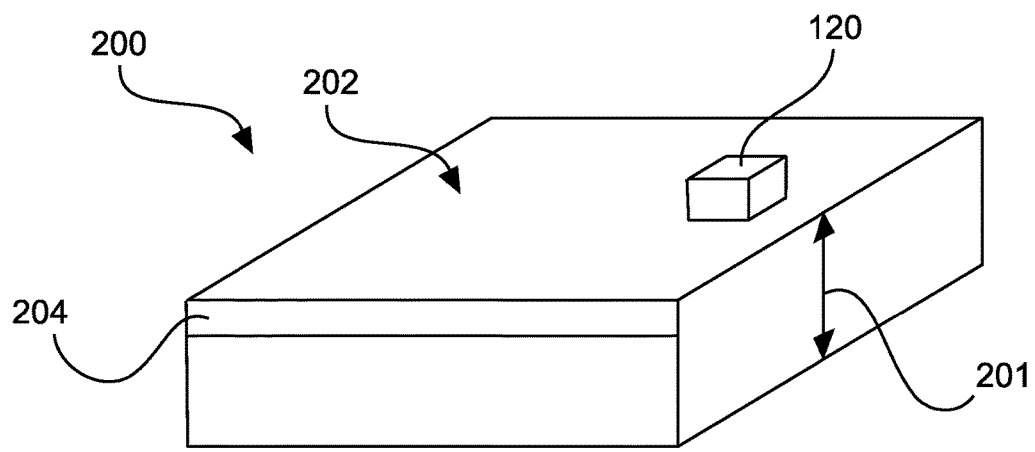
FIG. 2 shows a schematic representation of a material according to an additional embodiment, shown as an example.

FIG. 2 shows a material 200 with a sensor unit 120, which is disposed on the surface 202 of the material. The signal transmission element is not shown in FIG. 2 for reasons relating to a better presentation, but can be disposed on the surface 202 or in the surface layer 204, as well as extend over the entire material thickness 201 of the material 200.

The surface layer 204 can have a thickness or depth ranging from a few micrometers (μm) to some millimeters (mm). The sensor unit 120 is mechanically coupled to the surface 202 of the material and/or is fastened to the surface.

Figure 3:
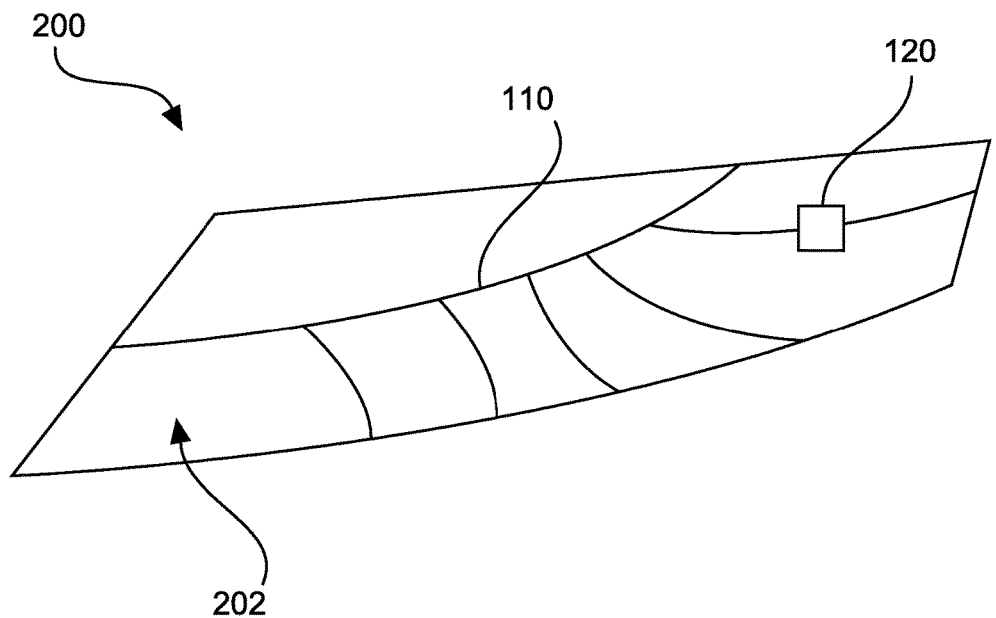
FIG. 3 shows a schematic representation of a material according to another embodiment, shown as an example.

FIG. 3 shows a material 200 in the form of an airplane wing. In this case the signal transmission element 110 comprising a plurality of conductor tracks or more specifically conductor track section is disposed on the surface 202 of the airplane wing. A sensor unit 120 is also disposed on the surface 202 and is electrically and/or thermally coupled to a conductor track of the signal transmission element 110.

It should be noted that the structural health monitoring system can have a plurality of sensor units 120, which are coupled to the signal transmission element 110. In this case the signals can be transmitted from a first sensor unit to a second sensor unit. Owing to the arrangement of several sensor units at different locations, the transmission function of the different conductor track sections can be checked or more specifically can be monitored, so that any structural defects that may occur can be localized.

The conductor tracks of the signal transmission element 110 can be disposed, in particular, at locations of the material that are subject to high mechanical stress, for example, in the region with high surface tensions or high bending forces or stresses due to vibration.

Figure 4:
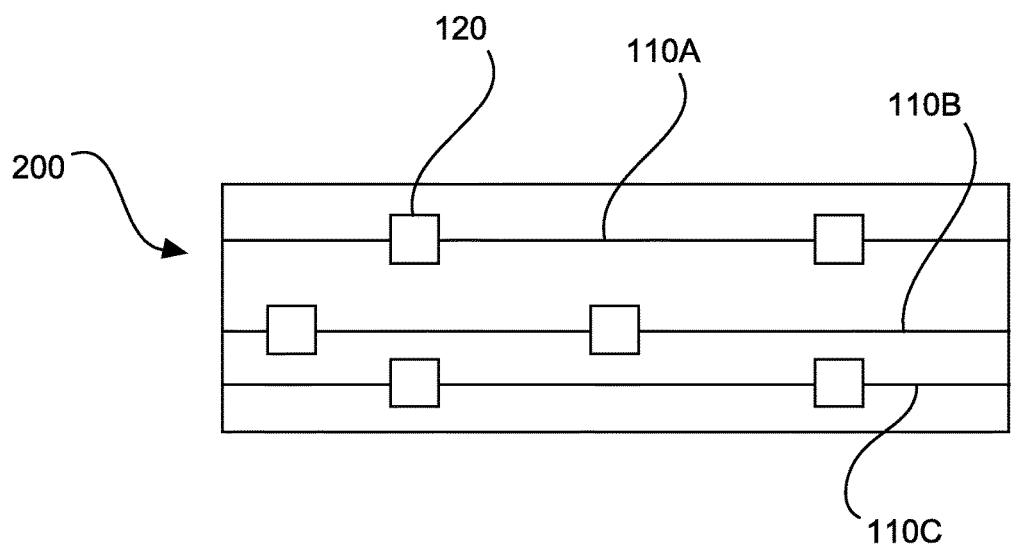
FIG. 4 shows a schematic representation of a material according to an additional embodiment, shown as an example.

FIG. 4 shows a material 200 with a structural health monitoring system comprising a signal transmission element 110 that has three conductor tracks 110A, 110B, 110C that are separated from each other. In this case each conductor track has two sensor units 120.

Thus, the transmission function of each of the three conductor tracks can be checked separately, because a first sensor unit feeds in a signal that is received and evaluated by the second sensor unit.

The signal that was sent can be transmitted from the first sensor unit to the second sensor unit over an additional transmission path, so that the receiving sensor unit can determine the transmission function from the actually sent signal and the received signal. As an alternative, a previously specified sequence of signals can be sent; and the second sensor unit knows this signal sequence, so that the transmission function can be determined without an additional transmission of the transmission signal sequence.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

LIST OF REFERENCE NUMERALS 100 structural health monitoring system
110 signal transmission element
120 sensor unit
200 material
201 material thickness
202 surface
204 surface layer

What is claimed is:

1. A metallic material, comprising:
   structural health monitoring system, which comprises
   a signal transmission element, which includes carbon nanotubes; and
   a sensor unit with a signal generator and a signal receiver,
   wherein the signal generator is configured to feed a first signal into the signal transmission element and wherein the signal receiver is configured to read out a second signal from the signal transmission element,
   wherein the second signal is an output signal which is the result of a transmission function of the signal transmission element being applied to the first signal.

2. The metallic material of claim 1, wherein
   the first signal and the second signal each contain an electrical signal component, and
   a ratio of the first signal to the second signal determines an electrical transmission function of the signal transmission element.

3. The metallic material of claim 1, wherein
   the first signal and the second signal each contain a thermal signal component, and
   a ratio of the first signal to the second signal determines a thermal transmission function of the signal transmission element.

4. The metallic material of claim 1, wherein
   the signal transmission element has a plurality of transmission lines made of carbon nanotubes, and
   at least one of the plurality of transmission lines is coupled to the sensor unit.

5. The metallic material of claim 4, wherein a first of the plurality of transmission lines crosses a second of the plurality of transmission lines, so that the signal transmission element is formed in a reticular manner.

6. The metallic material of claim 1, wherein the signal transmission element is a continuous surface.

7. The metallic material of claim 1, wherein the signal transmission element is disposed on a surface of the material.

8. The metallic material of claim 1, wherein the signal transmission element is disposed in a surface layer of the material.

9. The metallic material of claim 1, wherein the signal transmission element is distributed over an entire material thickness of the material.

10. A method for producing a metallic material, the method comprising:
    producing the metallic material with a structural health monitoring system, which comprises
    a signal transmission element, which includes carbon nanotubes; and
    a sensor unit with a signal generator and a signal receiver,
    wherein the signal generator is configured to feed a first signal into the signal transmission element and wherein the signal receiver is configured to read out a second signal from the signal transmission element,
    wherein the second signal is an output signal which is the result of a transmission function of the signal transmission element being applied to the first signal,
    wherein the signal transmission element is incorporated in the material by rolling in, adhesive bonding, or spraying.

11. The method of claim 10, wherein the signal transmission element is used as a weld filler material or as a powder metallurgy preform material in the production of the material.

12. The method of claim 10, wherein the signal transmission element is sewn, woven or knitted into the material.

13. The method of claim 10, wherein the signal transmission element is applied to the material as a coating layer.

14. The method of claim 10, wherein the signal transmission element is stirred individually or as a weld filler material into a surface of a workpiece or into friction stir weld seams.

* * * * *